United States Patent [19]

Hrebeniuk

[11] Patent Number: Plant 7,020

[45] Date of Patent: Sep. 5, 1989

[54] DISTINCT VARIETY OF POINSETTIA NAMED H519C

[76] Inventor: Alexander Hrebeniuk, R.D. #1, Box 118, Sugar Run, Pa. 18846

[21] Appl. No.: 178,333

[22] Filed: Apr. 6, 1988

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Webb, Burden, Ziesenheim & Webb

[57] ABSTRACT

A poinsettia plant named H519C particularly characterized by its dark bright red and fade resistant bracts, shiny leaves which are dark green and which lighten on maturity, plentiful bracts which continue to develop even after the Cyathia have dropped, fluffy and compact triple layer, habit and long lasting keeping qualities, and parts therefor.

1 Drawing Sheet

BACKGROUND OF THE NEW PLANT

The present invention comprises a new and distinct cultivar of *Euphorbia pulcherrima* known by the varietal name H519C. The new cultivar was developed in a breeding program and is a seedling resulting from the cross of the seed parent V14 (Ecke U.S. Plant Pat. No. 4,384) and the pollen parent H518 (Dynasty) (plant patent pending).

The new cultivar was discovered in November of 1985 in Sugar Run, Pa.; was first asexually reproduced by cuttings in May of 1986 in Sugar Run, Pa. and has been repeatedly asexually reproduced by cuttings at Sugar Run, Pa. Continued observations of the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Eight week response time under black cloth.
2. Four to six breaks after pinch.
3. May be grown single stem or pinch.
4. Top leaves are very dark green.
5. Mature leaves are slightly lighter.
6. Petioles are very dark red and shiny and darker than Red Group 46A.
7. Veins on leaves on top are shiny and lighter green; veins on bottom are light green.
8. Stems on bottom are green and on top are redish-green.
9. Bracts are dark bright red and very resistant to fade.
10. The centers of the bloom are very tight and medium large; Cyathia stay up to (6) weeks.
11. Red bracts continue to develop even after the Cyathia have dropped.
12. Bloom has three to four layers of bracts of the fluffy type.
13. Up to twenty eight (28) bracts have been developed on a fully developed bloom.
14. The largest bloom size measured on a single stem plant has been 18–19 inches in diameter.
15. Bracts range in size from 5 cm to 13 cm wide and 8 to 21 cm long.

16. In normal blooming, the new cultivar shows color in October and the bracts are fully developed by the end of November.
17. Responds well to the growth regulator Cycocel.
18. Plants keep up to three months under standard room temperatures. When grown at a temperature of 65° F., the fully bloomed flower retains its beauty and life at a temperature of 60° F. and has non-dropping foliage.
19. Plants ship well and are very long lasting.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight week plants. The color readings were determined at 1 p.m. on Feb. 3, 1988 under natural daylight at Sugar Run, Pa. Color references are primarily to the R.H.S. Colour Chart of The Royal Horticultural Society of London.

The plant:

*Form.*—Triple.

*Growth habit.*—Fluffy and very compact; taller than V-14.

*Rooting.*—Very fast.

*Blooming season.*—Eight weeks beginning at the end of October and the bracts are fully developed by end of November.

*Blooming habit.*—Large bracts in triple layer.

Foliage:

*Size.*—9 to 12 cm. wide and 11 to 15 cm long.

*Quantity.*—Up to fourteen leaves per stem depending on culture.

*Color.*—New foliage — Upper side, Green Group 139A. Under side, Green Group 139B. Old Foliage — Upper side, Green Group 138A. Under Side, Green Group 138B. Leaf Petiole — Red Group 46A.

*Shape.*—On single plant upper leaves tend to be heart shaped with lower leaves generally oak shaped; on pinch plant all oak shaped.

*Texture.*—The upper side is velvety and the under side is rough because of veins.

*Edge of margin.*—Wavy.

*Aspect.*—Varies from nearly horizontal to upwardly and downwardly inclined.

*Veins.*—Midrib to margin.

*Disease resistance.*—Resistant to botrytis.

Flower: (Cyathia).

*Borne.*—Single, very compact inflorescence.

*Quantity.*—No more than 16; each one has a nectary.

*Color.*—Varies widely depending on stage of development; when mature the color generally is orange to orange-red with the green being Green Group 145A.

Bracts:

*Size.*—5 cm. wide and 8 cm. long when immature to 13 cm. wide and 21 cm. long when fully grown.

*Veins.*—Midrib to margin.

*Quantity.*—28 leaves producing a tight fluffy bloom.

*Color.*—Top: Red Group 46B. Veins: Red Group 46A. Bottom: Red Group 46C. The difference in vein color and bract color becomes inconspicuous at a distance and is not photographically detectable at reasonable distances using conventional techniques.

*Resistance to fade.*—excellent for basket.

Reproductive organs: Typical for poinsettia cultivars.

I claim:

1. A new and distinct variety of poinsettia plant as herein shown and described, and particularly characterized by its dark bright red and fade resistant bracts, shiny leaves which are dark green and which lighten on maturity, plentiful bracts which continue to develop even after the Cyathia have dropped, fluffy and compact triple layer, habit and long lasting keeping qualities.

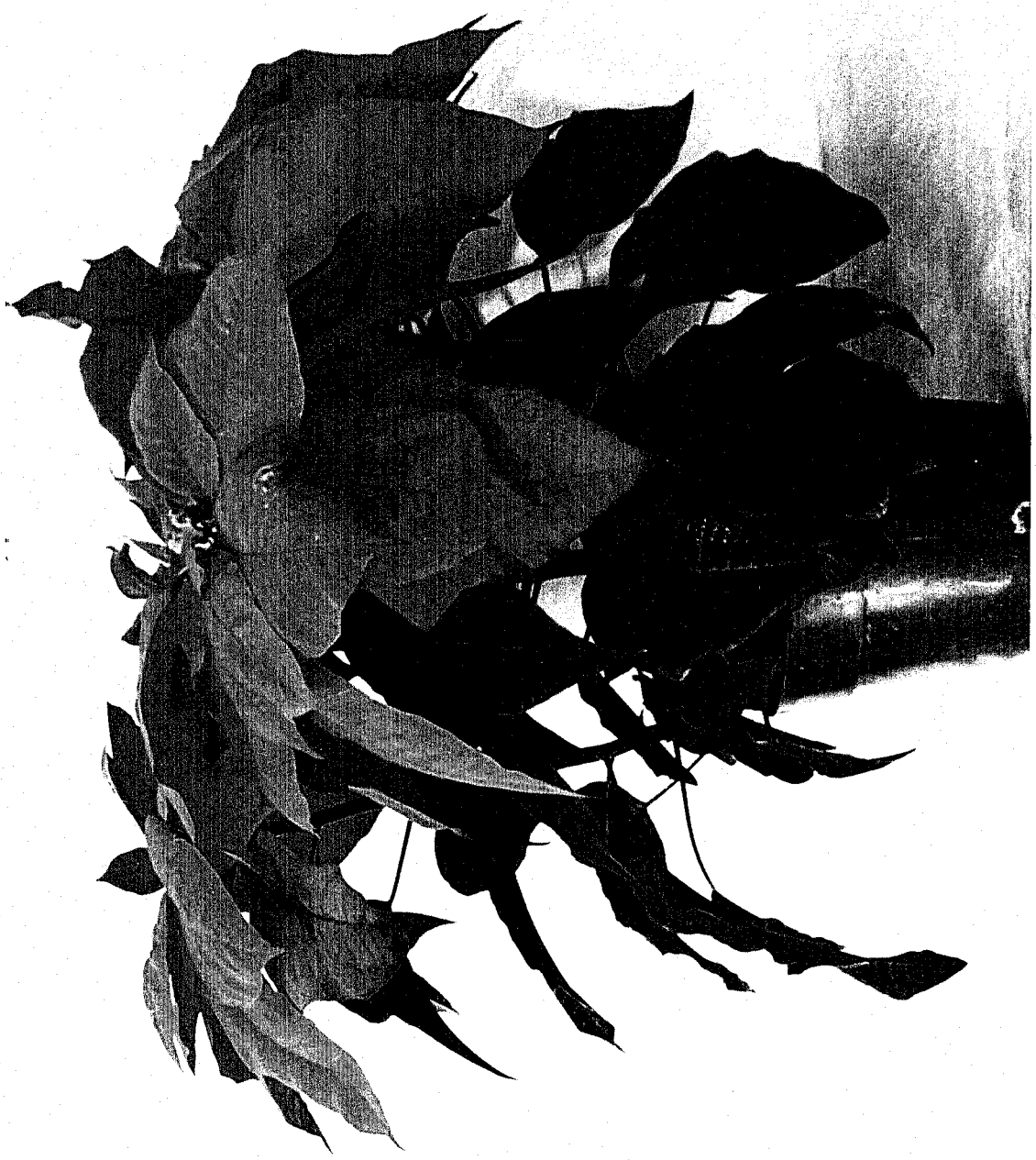

* * * * *